(12) United States Patent
Qin

(10) Patent No.: US 12,019,062 B2
(45) Date of Patent: *Jun. 25, 2024

(54) TEST PAPER BOX AND INTELLIGENT TOILET CONTAINING SAME

(71) Applicant: Shanghai Kohler Electronics, Ltd., Shanghai (CN)

(72) Inventor: Zhiyu Qin, Beijing (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/742,204

(22) Filed: May 11, 2022

(65) Prior Publication Data

US 2022/0268757 A1 Aug. 25, 2022

Related U.S. Application Data

(63) Continuation of application No. 16/099,640, filed as application No. PCT/CN2016/103186 on Oct. 25, 2016, now Pat. No. 11,353,447.

(30) Foreign Application Priority Data

May 10, 2016 (CN) .......................... 201610304863.7

(51) Int. Cl.
*B65D 83/08* (2006.01)
*G01N 33/48* (2006.01)
(Continued)

(52) U.S. Cl.
CPC ....... *G01N 33/48757* (2013.01); *B65D 83/08* (2013.01); *G01N 33/48* (2013.01); *G01N 33/493* (2013.01)

(58) Field of Classification Search
CPC ................ G01N 33/493; G01N 33/48; G01N 33/48757; G01N 33/4875; B65D 83/08;
(Continued)

(56) References Cited

U.S. PATENT DOCUMENTS 1,328,664 A 1/1920 Fritsche
2,027,673 A 1/1936 Broeren
(Continued)

FOREIGN PATENT DOCUMENTS

CN 101266241 A 9/2008
CN 102590536 A 7/2012
(Continued)

OTHER PUBLICATIONS

English language summary of Japanese Notification of Reasons of Refusal, App. No. 2019-510733, Kohler Co. (dated Apr. 13, 2020).
(Continued)

*Primary Examiner* — Rafael A Ortiz
(74) *Attorney, Agent, or Firm* — Lempia Summerfield Katz LLC

(57) ABSTRACT

The present invention provides a test paper box and a smart toilet containing same. The test paper box comprises a support and a housing arranged at the outside of the support. The support comprises a base and an elongated cavity arranged at the base for storing test paper. The base is provided with a through hole arranged at a location corresponding to a bottom surface of the elongated cavity. A paper-receiving slot is arranged below the through hole. The paper-receiving slot is fixed to the bottom of the base to receive the bottommost piece of test paper exposed from the elongated cavity, and the paper-receiving slot is provided with a paper outlet. The test paper box can be attached and
(Continued)

detached conveniently, delivers test paper smoothly, can be replaced easily, has low costs, and is suitable for smart toilets.

15 Claims, 2 Drawing Sheets

(51) Int. Cl.
 *G01N 33/487* (2006.01)
 *G01N 33/493* (2006.01)
(58) Field of Classification Search
 CPC .... B65D 81/26; A47K 13/165; A47K 13/145; A47K 13/16; A47K 10/42; A47K 10/32; A47K 10/26; A47K 10/24; A47K 10/16; A47K 10/08; A47K 10/025; A47K 10/00
 USPC .... 206/204; 221/229, 50, 282, 192, 191, 92, 221/93, 45, 46, 33, 36, 37; 4/695, 313, 4/321, 300.1, 244.2, 244.1, 243.3, 243.2, 4/243.1, 340–342
 See application file for complete search history.

(56) References Cited

U.S. PATENT DOCUMENTS

| | | | |
|---|---|---|---|
| 2,123,012 | A | 7/1938 | Kreutzig |
| 2,712,654 | A | 7/1955 | Batlas et al. |
| 3,007,177 | A | 11/1961 | Jackson et al. |
| 4,944,046 | A | 7/1990 | Huh et al. |
| 5,219,092 | A | 6/1993 | Morand |
| 5,337,897 | A * | 8/1994 | Yablans .............. B65D 83/0858 206/823 |
| 6,382,460 | B1 | 5/2002 | Gonzalez |
| 8,166,579 | B2 | 5/2012 | Mehta |
| 2005/0166307 | A1 | 8/2005 | Parks et al. |
| 2005/0281706 | A1* | 12/2005 | Funke .............. G01N 33/48757 422/430 |
| 2006/0261076 | A1 | 11/2006 | Anderson |
| 2006/0283873 | A1 | 12/2006 | Bostic |
| 2007/0084749 | A1* | 4/2007 | Demelo ........... G01N 33/48778 206/569 |
| 2007/0220664 | A1 | 9/2007 | Getahun et al. |
| 2008/0217354 | A1 | 9/2008 | Newman et al. |
| 2009/0277920 | A1 | 11/2009 | Cittadino et al. |
| 2011/0127176 | A1* | 6/2011 | Chang .................. B65D 81/266 206/204 |
| 2011/0131714 | A1 | 6/2011 | Remijn et al. |
| 2012/0193246 | A1* | 8/2012 | Chang .................. B65D 51/245 206/204 |
| 2013/0220844 | A1* | 8/2013 | Logel .................. B65D 43/162 206/204 |
| 2015/0291338 | A1* | 10/2015 | Chen .................... B65D 51/244 206/204 |
| 2017/0108486 | A1* | 4/2017 | Joseph .................. B65D 53/02 |
| 2018/0020844 | A1 | 1/2018 | Stuttgen et al. |

FOREIGN PATENT DOCUMENTS

| | | |
|---|---|---|
| CN | 103496515 A | 1/2014 |
| CN | 203379063 U | 1/2014 |
| CN | 105800126 A | 7/2016 |
| CN | 205633666 U | 10/2016 |
| DE | 20109498 U1 | 3/2002 |
| JP | 1988091562 | 6/1989 |
| JP | 2003344424 A | 12/2003 |
| JP | 2004505244 A | 2/2004 |
| JP | 2008216258 A | 9/2008 |
| WO | 200208753 A2 | 1/2002 |

OTHER PUBLICATIONS

International Search Report re Application No. PCT/CN2016/103186; 11 pgs, dated Feb. 16, 2017.
Notice of Preliminary Rejection for KR 10-2018-7035418 dated Dec. 18, 2019, with English translation 9 pages.

* cited by examiner

TEST PAPER BOX AND INTELLIGENT TOILET CONTAINING SAME

CROSS REFERENCE TO OTHER APPLICATIONS

This application is a continuation under 35 U.S.C § 120 and 37 C.F.R. § 1.53(b) of U.S. patent application Ser. No. 16/099,640, filed Nov. 7, 2018, which is a national stage entry of PCT/CN2016/103186, filed Oct. 25, 2016, which claims the benefit and priority of Chinese Patent Application No. 201610304863.7, filed May 10, 2016, and each of which is hereby incorporated by reference in its entirety.

TECHNICAL FIELD

The present invention relates to the field of smart toilet, and particularly to a test paper box and a smart toilet containing same.

BACKGROUND

With the improvement of people's life demands, smart toilets are increasingly favored by consumers. Currently, the smart toilets generally have the functions of cleaning, heating, sterilizing, or the like, and some toilets are added with a urine detection function, The function is generally realized by detecting real-time urine through a test paper stored in the smart toilet in advance. Due to the special environment condition of the smart toilet (such as smaller space, humidity, etc.), the storage and replacement issues of the test paper need to be solved. Therefore, a novel test paper box that is convenient in disassembly and assembly, easy in paper delivery, easy in replacement, and low in cost is designed, which can greatly simplify the operating method of the smart toilet while ensuring the accuracy of the urine detection.

SUMMARY

One object of the present invention is to provide a test paper box that is convenient in disassembly and assembly, easy in paper delivery, easy in replacement, and low in cost, and is more suitable for a smart toilet.

Another object of the present invention is to provide a smart toilet containing the test paper box.

In order to achieve the objects above, the following technical solutions are employed in the present invention.

A test paper box comprises a support and a housing outside the support, the support comprises a base and an elongated cavity arranged at the base for storing the test paper, the base is provided with a through hole disposed at a position corresponding to a bottom surface of the elongated cavity, a paper-receiving slot is arranged below the through hole, the paper-receiving slot is fixed to the bottom of the base to receive the bottommost piece of test paper exposed from the elongated cavity, and a paper outlet is arranged at the paper-receiving slot.

As further improvement of the present invention, a side wall of the elongated cavity is provided with air hole, and a dampproof component is provided at the air hole.

The dampproof component can be a desiccant bag, and the desiccant bag is fixed between the side wall of the elongated cavity and the housing.

The base of the support is provided with a clamping slot. The housing is provided with a locking tongue at inner wall. The support and the housing are fixed together through the fitting between the clamping slot and the locking tongue.

The housing is a shell with an opening at the bottom. The shell is sheathed on the elongated cavity of the support, and the opening at the bottom of the shell is covered by the base of the support.

A paper inlet is provided on the top of the elongated cavity. And a covering structure is provided on the top of the shell for matching with the paper inlet.

The shell of the housing is further provided with a positioning slot for installation.

The test paper box further comprises a seal assembly, and the seal assembly comprises a seal platform raised surrounding the through hole on the base, and a gasket for matching with the seal platform to seal the paper-receiving slot.

A smart toilet comprises a paper feeding module which comprises a lifting mechanism and a pushing mechanism, and further comprises the test paper box, wherein the test paper box is provided with a clamping slot for being connected to the lifting mechanism, and when the lifting mechanism lifts the test paper box to expose the paper-receiving slot of the test paper box, the pushing mechanism is used for pushing out the test paper in the paper-receiving slot from the paper outlet.

As a further improvement of the present invention, the clamping slot comprises grooves arranged at two ends of the base of the test paper box and grooves arranged at two ends of the housing.

By using the above technical solution, the present invention at least has the following advantages.

(1) With the paper-receiving slot arranged at the bottom of the base, the test paper box is convenient in paper delivery, do not readily jam and easy to push out.

(2) With the air hole and the dampproof component provided at the air hole, an effective dampproof protection of the test paper in the test paper box is obtained, thereby avoiding invalidation.

(3) With the snap-fit between the support and the housing and the opening of the housing being covered by the base of the support, the advantages of convenient in disassembly and assembly, easy in replacement, simple in structure and low in cost can be obtained.

(4) The covering structure is provided on the top of the inner surface of the housing for matching with the paper inlet, which further improves the sealing property, (5) The shell of the housing is provided with the positioning slot for installation, which avoids reverse direction during replacement or installation.

(6) The seal assembly ensures the good sealing of the test paper box under a non-use state, which avoids the influence of damp environment when the test paper box is used in the smart toilet.

In conclusion, the test paper box of the present invention is good in sealing property, convenient in disassembly and assembly, easy in paper delivery, easy in replacement, and low in cost, and is more suitable for the smart toilet.

BRIEF DESCRIPTION OF THE FIGURES

The foregoing description is merely a summary of the technical solutions of the present invention. To understand the technical means of the present invention more clearly, the present invention is further described in detail with reference to the figures and the detailed embodiments hereinafter.

DETAILED DESCRIPTION

The present invention provides a test paper box that is good in sealing property, convenient in disassembly and assembly, easy in paper delivery, easy in replacement, and low in cost.

Figure 1:
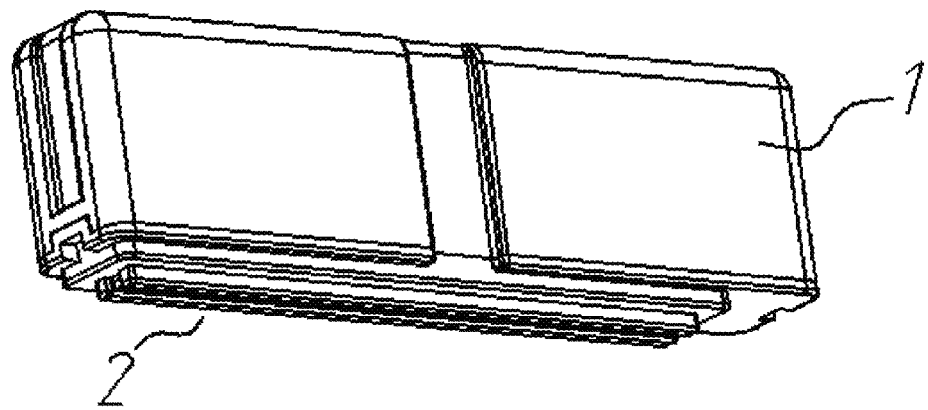
FIG. 1 and FIG. 4 are schematic diagrams of the whole structure of the test paper box according to the present invention from different views.
Figure 2:
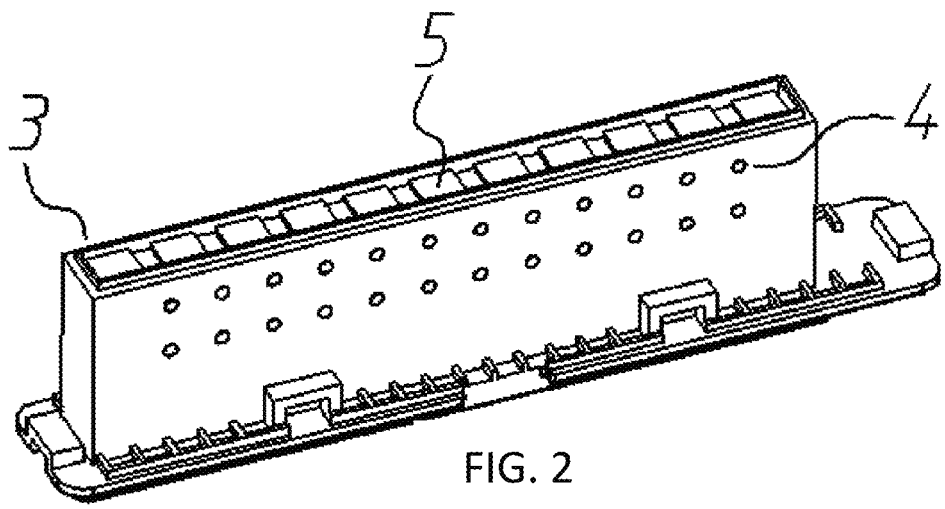
FIG. 2 is a schematic diagram of the support.

As shown in FIGS. 1 and 2, the test paper box of the present invention comprises a housing 1 and a support 2. The support 2 comprises a base and an elongated cavity arranged at the base for storing test paper 5, and the test paper 5 is filled into the elongated cavity through a paper inlet 3 at a top of the elongated cavity. After the test paper 5 is arranged according to quality, the housing 1 is sheathed on the support 2 from top to bottom.

Figure 5:
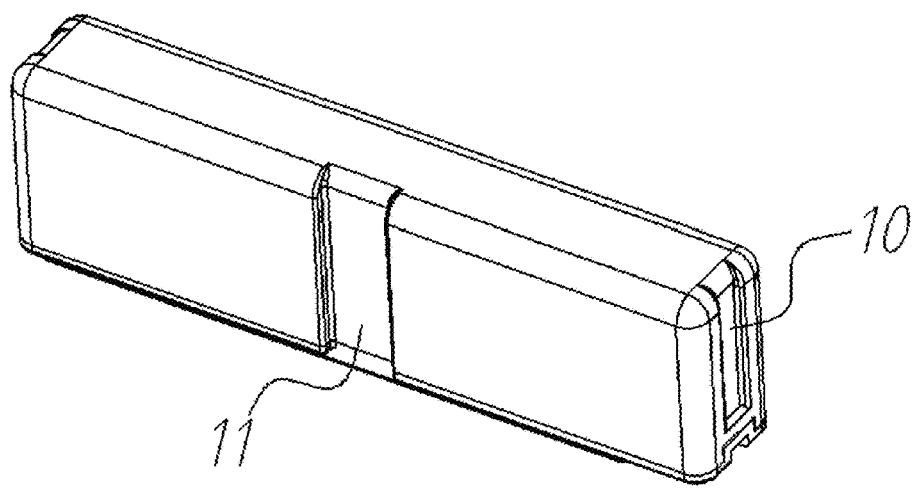
FIG. 5 is a perspective view of the housing.
Figure 6:
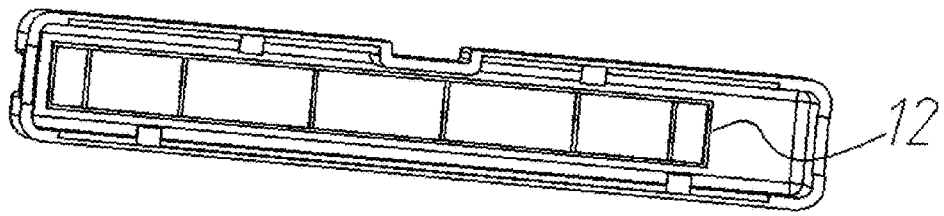
FIG. 6 is a schematic diagram of the internal structure of the housing.

As shown in FIGS. 5 and 6, the housing 1 is a shell with an opening at the bottom, and the shell is sheathed on the elongated cavity of the support 2. A covering structure 12 is provided on the top of the inner surface of the housing 1 for matching with the paper inlet 3 arranged at the top of the elongated cavity so as to seal the test paper 5 in the elongated cavity of the support 2.

With reference to FIGS. 2 and 6, the housing 1 and the support 2 are fixed together through a snap-fit. Specifically, a clamping slot is provided on the base of the support 2, and a locking tongue is provided on the inner wall of the housing 1. The support 2 and the housing 1 are fixed together through the snap-fit between the clamping slot and the locking tongue, so that the opening at the bottom of the housing 1 is covered by the base of the support 2.

Figure 3:
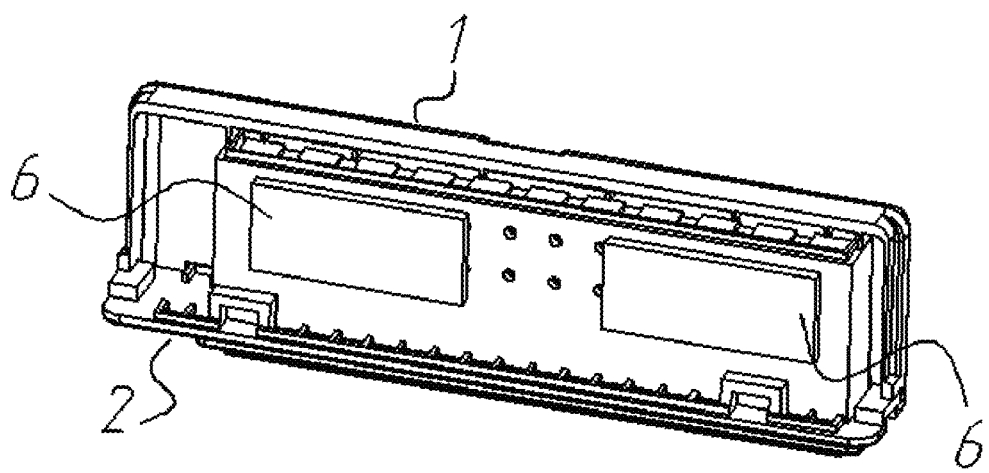
FIG. 3 is a schematic diagram of a part of the test paper box according to the present invention.

With reference to FIGS. 2 and 3, some air holes 4 are disposed around the elongated cavity of the support 2, and the air holes 4 can be disposed in the side walls of the elongated cavity. A dampproof component is provided at the air holes 4 for dampproof protection of the test paper in the elongated cavity. Preferably, the dampproof component can be a desiccant bag 6, the desiccant bag 6 is fixed between the housing 1 and the elongated cavity, and a plurality of the desiccant bags 6 can be disposed as appropriate.

Figure 4:
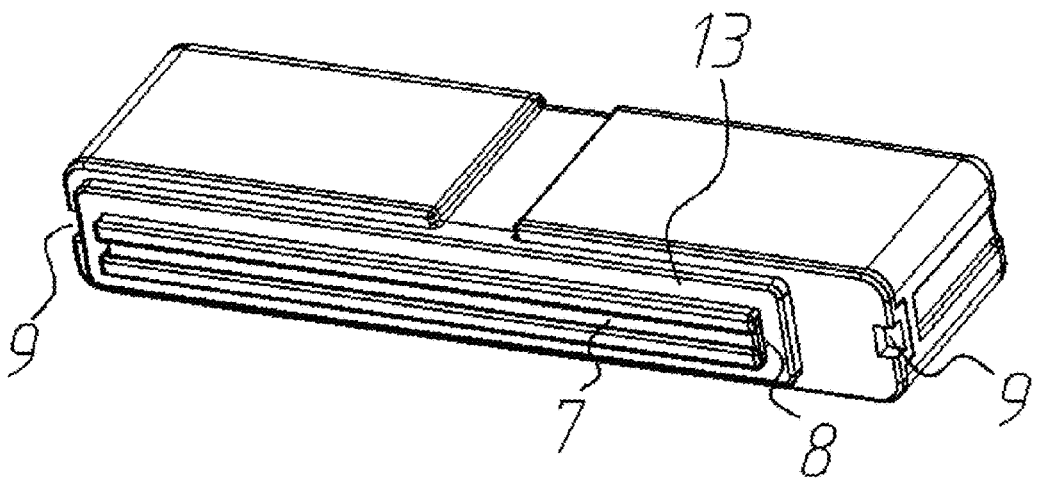

With reference to FIG. 4, the base of the support 2 is provided with a through hole disposed at a position corresponding to a bottom surface of the elongated cavity, and a elongated paper-receiving slot 7 is disposed below the through hole, the paper-receiving slot 7 is fixed to the bottom of the base to receive the bottommost piece of test paper exposed from the elongated cavity, and one end of the paper-receiving slot 7 is a paper outlet 8. In addition, at the bottom of the base is further provided with a seal platform 13 raised surrounding the through hole on the base. The seal platform 13 can be provided as a plastic platform integrated with the base of the test paper box, which is used for being mutually matched with a gasket (not shown in the figure) located below the paper-receiving slot 7, so as to seal the entire paper-receiving slot 7, and the seal assembly formed by the seal platform 13 and the gasket effectively prevents the test paper from invalidation caused by damp exterior during use.

The present invention further provides a smart toilet containing the test paper box above. The smart toilet comprises a paper feeding module, which comprises a lifting mechanism and a pushing mechanism for matching with the test paper box. With reference to FIGS. 4 and 5, the test paper box is provided with clamping slots for connecting with the lifting mechanism, which comprises clamping slots 9 arranged at two ends of the base and clamping slots 10 arranged at two ends of the housing 1. For example, the clamping slots 9 can be used for lifting the test paper box, and the clamping slots 10 can be used for descending the test paper box.

When the paper delivery of the test paper box is needed during actual use, the test paper box needs to be lifted by the lifting mechanism firstly and the paper-receiving slot 7 of the test paper box is revealed, and then the pushing mechanism is used for horizontally pushing out the test paper from the paper-receiving slot 7. Specifically, the pushing mechanism is provided with a pulling rod, the pulling rod can enter through one end of the paper-receiving slot 7 and push out the test paper from the paper outlet 8 at the other end of the paper-receiving slot 7 after passing through the paper-receiving slot 7. The test paper pushed out is the bottommost piece of test paper stored in the elongated test paper cavity. After the test paper is pushed out, the upper piece of test paper will fall into the paper-receiving slot 7 by the effect of the self-weight, Next time when use, the pushing mechanism will enter through the paper-receiving slot 7 again to push out the test paper. Since a plurality of new test paper is stored in the elongated cavity, continuous use of the test paper is available; after the test paper is used up, new test paper can be supplemented again, or the empty test paper box can be abandoned, and new test paper box is directly replaced. In order to prevent the newly installed test paper box from reversing left and right, the housing 1 of the test paper box is further provided with a positioning slot 11 for determining a placement direction of the test paper box (FIG. 5).

If the test paper is not used, and the test paper box needs to be placed stationarily, then test paper box is descended through the lifting mechanism, the bottom of the test paper box is pressed on the said gasket, and the paper-receiving slot 7 is completely sealed through the matching of the gasket with the seal platform 13, to prevent the test paper from being affected with damp. The gasket can be arranged according to the actual installation position of the test paper box, for example, the smart toilet can be independently provided with a special gasket installation support.

The foregoing description is merely preferred embodiments of the present invention, but is not intended to limit the present invention in any form, and any simple amendments, equivalent changes or modifications made by those skilled in the art using the technical contents disclosed above shall all fall within the protection scope of the present invention.

What is claimed is:

1. A test paper box, comprising:
   a support comprising:
      a base; and
      an elongated cavity configured to store test paper, the elongated cavity having a side wall that is provided with an air hole and a dampproof component arranged along an exterior of the side wall at the air hole opposite the test paper relative to the side wall;
   a shell with an opening at a bottom of the shell, the shell sheathing the elongated cavity of the support,
   wherein the support further comprises a clamping slot configured to receive a locking tongue of the shell so that the opening at the bottom of the shell is covered by the base of the support and wherein the clamping slot is configured to facilitate lifting the shell with respect to the support, and a paper outlet from which a piece of test paper stored in the elongated cavity is pushed out when the shell is lifted via the clamping slot.

2. The test paper box of claim 1, further comprising a paper-receiving slot that is provided below the elongated cavity and is fixed to a bottom of the base to receive the piece of test paper exposed from the elongated cavity, and wherein the paper outlet is provided at an end of the paper receiving slot.

3. The test paper box of claim 1, wherein the dampproof component comprises a desiccant bag.

4. The test paper box of claim 3, wherein the desiccant bag is situated between the shell and the elongated cavity.

5. The test paper box of claim 1, wherein a top of the elongated cavity is provided with a paper inlet and a covering structure that is provided on a top of the shell, wherein the covering structure is configured to match with the paper inlet.

6. The test paper box of claim 1, wherein the shell is further provided with a positioning slot for installation in a toilet.

7. The test paper box of claim 1, further comprising a seal platform raised relative to the base and surrounding a through hole on the base.

8. A test paper box, comprising:
a support comprising:
  a base; and
  a cavity configured to store test paper, the cavity having a side wall that is provided with an air hole and a dampproof component located along an exterior of the side wall at the air hole opposite the test paper relative to the side wall;
a shell with an opening at a bottom of the shell, the shell sheathing the cavity of the support, the opening being covered by the base of the support, and the shell comprising a positioning slot for installation of the test paper box in a toilet;
wherein the support further comprises a clamping slot configured to receive a locking tongue of the shell so that the opening at the bottom of the shell is covered by the base of the support and wherein the clamping slot is configured to facilitate lifting the shell with respect to the support, and
a paper outlet from which a piece of test paper stored in the cavity is pushed out when the shell is lifted via the clamping slot.

9. The test paper box of claim 8, wherein a top of the cavity is provided with a paper inlet located at the top of the cavity and sized to receive test paper for storing in the cavity.

10. The test paper box of claim 9, further comprising a covering structure that is configured to match with the paper inlet.

11. The test paper box of claim 8, further comprising a seal platform raised relative to the base and surrounding a through hole of the base from which test paper of the cavity passes through.

12. The test paper box of claim 8, wherein the cavity is provided with a paper inlet.

13. The test paper box of claim 8, further comprising a paper-receiving slot that is provided below the cavity and is fixed to a bottom of the base to receive the piece of test paper exposed from the cavity, and wherein the paper outlet is provided at an end of the paper receiving slot.

14. The test paper box of claim 8, wherein the dampproof component is situated between the shell and the cavity at the air hole.

15. A test paper box, comprising:
a support comprising:
  a base; and
  an elongated cavity configured to store test paper, the elongated cavity having a side wall that is provided with an air hole and a dampproof component arranged along an exterior of the side wall at the air hole opposite the test paper relative to the side wall;
a shell with an opening at a bottom of the shell, the shell sheathing the elongated cavity of the support,
wherein the support further comprises a clamping slot configured to receive a locking tongue of the shell so that the opening at the bottom of the shell is covered by the base of the support, and
a paper outlet from which a piece of test paper stored in the elongated cavity is pushed out.

\* \* \* \* \*